(12) United States Patent
Richards et al.

(10) Patent No.: US 7,608,238 B2
(45) Date of Patent: Oct. 27, 2009

(54) NANOSHEETS OF MGO PROCESSING THE 111 PLANE

(75) Inventors: Ryan Richards, Bremen (DE); Kake Zhu, Shanghai (CN); Christian Kubel, Bremen (DE)

(73) Assignee: International University Bremen GmbH, Bremen (DE)

( * ) Notice: Subject to any disclaimer, the term of this patent is extended or adjusted under 35 U.S.C. 154(b) by 555 days.

(21) Appl. No.: 11/356,314

(22) Filed: Feb. 17, 2006

(65) Prior Publication Data

US 2007/0196266 A1    Aug. 23, 2007

(51) Int. Cl.
*C01F 5/02* (2006.01)
*C01F 5/06* (2006.01)
(52) U.S. Cl. .................. 423/635; 423/636; 502/439; 501/108
(58) Field of Classification Search ............ 423/635, 423/636; 501/108; 502/439; C01F 5/02
See application file for complete search history.

(56) References Cited

OTHER PUBLICATIONS

Plass, R. et al., "Cyclic Ozone Identified in Magnesium Oxide (111) Surface Reconstruction" Physical Review Letters 1998, 81, 4891-4894.*
Wander et al., "Stability of rocksalt polar surfaces: An ab initio study of MgO(111) and NiO(111)", Physical Review B 2003, 68, No. 233405.*
Plass et al. "Morphology of MgO(111) surfaces artifacts associated with the faceting of polar oxide surfaces into neutral surfaces", Surface Science 414 (1998) 26-37.*

* cited by examiner

*Primary Examiner*—Roy King
*Assistant Examiner*—Rebecca Lee
(74) *Attorney, Agent, or Firm*—Sughrue Mion, PLLC

(57) ABSTRACT

Periclase MgO having a nanosheet structure. The distance of the lattice planes in HRTEM is −0.24 nm-0.25 nm. Method of preparing periclase MgO having a nanosheet structure including preparation of $Mg(OCH_3)_2$ in methanol solution. 4-methoxy benzy alcohol (MBZ) or 4-nitro benzyl alcohol (NBZ) or a mixture thereof is added in a ration of Mg to MBZ and/or NBZ of at least 1. Water/methanol mixture is added to the system. Solvent removal and calcinations in air is performed of the mixture.

3 Claims, 20 Drawing Sheets

NANOSHEETS OF MGO PROCESSING THE 111 PLANE

FIELD OF THE INVENTION

The invention is related to a novel form of MgO possessing the (111) plane, preferably as so-called nanosheets, as well as to a method of manufacturing the same. In particular, the invention is related to the wet chemical preparation of such nanosheets via a preferential growth magnesium methoxide-benzyl alcohol method.

BACKGROND ART

MgO has a typical rocksalt structure with a high melting point, and high ionic character. Although the stoichiometry and crystallinity change little, the morphology can vary in shape, particle size and surface structure. The (100) face is unambiguously the most stable due to its low surface energy, therefore, it is normally a product after cleavage. However, the (111) surface is particularly interesting, because it possesses alternating polar monolayers of negatively charged oxygen anions and positively charged magnesium cations. Thus, a strong electrostatic field perpendicular to the (111) surface is created. Moreover, the cleavage energy of the surface, upon the ionic model, depends on the slab thickness (Tasker, P. W., *Journal of Physics C-Solid State Physics* 1979, 12, 4977-4984). Such a surface has provided a prototype for the study of surface structure and surface reactions of oxides, which drew great attention for both experimental and theoretical studies (Plass, R. et al., *Physical Review Letters* 1998, 81, 4891-4894; Plass, R. et al., *Surface Science* 1998, 414, 26-37; Wander, A. et al., *Physical Review* B 2003, 68, No. 233405; Zuo, J. M. et al., *Physical Review Letters* 1997, 78, 4777-4780; Refson, K. et al., *Physical Review* B 1995, 52, 10823-10826).

Preparations and studies of MgO (111) have thus far been limited to deposition on substrates such as NiO (111) or Ag (111) (Gajdardziska-Josifovska, M. et al., *Journal of Electron Microscopy* 2002, 51, S13-S25; Arita, R. et al., *Physical Review* B 2004, 69, No.235423; Subramanian, A. et al., *Physical Review Letters* 2004, 92, No. 026101), acid etching, ion bombardment, and electron beam annealing (1000° C.) in UHV, high temperature annealing (800° C.) in air and also after oxygen plasma cleaning and annealing in UHV and various other etching and reconstruction processes (Henrich, V. E., *Surface Science* 1976, 57, 385-392; Arita, R. et al., supra; Subramanian, A. et al. supra; Lazarov, V. K. et al., *Physical Review Letters* 2005, 94, 216101-1-216101-4; Lazarov, V. K. et al., *Physical Review* B 2005, 71, 216108-1-216108-4; Lazarov, V. K. et al. Gajdardziska-Josifovska, M. *Physical Review Letters* 2003, 90, 115434-1-115434-9).

The traditional method for preparation of MgO is the thermal decomposition of either magnesium salts or magnesium hydroxides, which results in inhomogeneity of morphology, crystallite size and low surface area (Green, J., *Journal of Materials Science* 1983, 18, 637-651; Kim, M. G. et al., *Journal of the American Ceramic Society* 1987, 70, 146-154).

Commercially available MgO is normally polycrystalline in nature and has a surface area of around 10-30 $m^2/g$. Many efforts have been exerted to prepare MgO of controlled shapes and morphologies. MgO aerogels are among the most well-known. Teichner (Teichner, S. J. et al., *Advances in Colloid and Interface Science* 1976, 5, 245-273) first developed MgO aerogel by using hydrolysis and condensation reactions of alkoxides.

Two types of nanocrystalline oxides have been prepared and thoroughly studied: a "conventional preparation" (CP), and an "aerogel preparation" (AP) (Utamapanya, S. et al., *Chemistry of Materials* 1991, 3, 175-181; Diao, Y. L. et al., *Chemistry of Materials* 2002,14, 362-368) (see FIG. 2). Nanocrystalline (AP) MgO was prepared by a modified aerogel procedure, yielding a fine, white powder of 400-500 $m^2/g$ and 4 nm average crystallite size. The conventionally prepared (CP) MgO is made up of ordered microcrystals with large exposed areas of the (100) face and possesses a surface area between 130-250 $m^2/g$. Klabunde found toluene (Utamapanya, S. et al., supra; Diao, Y. L. et al., supra; Ranjit, K. T. et al., supra) to be the most effective co-solvent for the formation of an aerogel of MgO which resulted in ~4 nm polyhedron crystallites rich in edge/corner sites with a surface area ranging from 300-500 $m^2/g$ (Richards, R. et al., *Journal of the American Chemical Society* 2000, 122, 4921-4925). Organic solvents with low and high dielectric constants (low dielectric constant solvents, i.e. hexane, benzene, ethyl benzene, propyl benzene, mesitylene; high dielectric constant solvents, i.e., N,N-dimethyl aniline, anisole, acetone, acetonitrile, N,N-DMF, DMSO) were also employed as co-solvents for the formation of magnesium hydroxide gels. It was found that different solvents could influence the gelation speed and subsequent porosity effectively, however, no differences in the crystalline phases magnesium oxide/hydroxide prepared in the methanol/toluene solvent system were observed (Ranjit, K. T. et al., supra).

Recently, it was reported that mesoporous carbon aerogel (Li, W. C. et al., *Chemistry of Materials* 2004, 16, 5676-5681) and hexagonal arrays of carbon (Roggenbuck, J. et al., *Journal of the American Chemical Society* 2005, 127, 1096-1097) can be employed as hard templates to shape the formation of MgO during thermal decomposition of magnesium nitrate thus resulting in ordered mesoporous MgO which mimics the template in structure and have a surface area of 150 and 306 $m^2/g$ respectively. More recently, Knoezinger and co-workers developed a Chemical Vapor Deposition (CVD) method which produces MgO cubes with controllable particle size, however, the surface of these cubes unanimously possess the (100) surface, which shows size-dependent optical properties (Stankic, S. et al., *Angew. Chem. Int. Ed.* 2005, 44, 4917-4920). These studies show the diversity and complexity of MgO in shape and particle size, however, as far as surface orientation is concerned, to our best knowledge neither selectivity nor controlled growth have been reported for substrate-free systems.

As the size of a particle decreases, the percentage of atoms residing on the surface increases. As an example, a study on different samples of MgO nanoparticles has revealed that for particles ~4 nm in diameter, ~30% of the atoms are surface atoms. (Koper, O. B. et al., *Chemistry of Materials* 1997, 9, 2468-2480). Of course, surface atoms/ions are expected to be more reactive than their bulk counterparts as a result of coordinative unsaturation. Because of this and the fact that the surface to volume ratio is large, it is not unusual to see unique behavior and characteristics for nanoparticles. This particle size effect is a characteristic of different nano-materials including metal oxides. MgO is widely used as a catalyst or catalyst support, ad-sorbent, or as an additive in refractories and paint, and may be applied in the semiconductor industry as a thin film intermediate for other metal oxides. The shape and size of crystalline MgO is highly influential on the adsorption properties and the configuration of surface species formed during chemical adsorption. For example, $SO_2$ has been found to interact with the surface of MgO aerogel nanocrystallites in a monodentate adsorption mode while larger MgO microcrystals favored a bidentate adsorption. (Lucas, E. et al., *Chemistry-a European Journal* 2001, 7, 2505-2510; Stark, J. V. et al., *Chemistry of Materials* 1996, 8, 1904-1912; Itoh, H. et al., *Chemistry of Materials* 1993, 5, 71-77). This selectivity is also found for acetylene in theoretical ab initio studies and solid state NMR experimental studies as well, no stable dissociation products on the flat (100)-like surface could be obtained theoretically or experimentally (Nicholas, J. B. et al., *Journal of the American Chemical Society* 1998, 120, 10471-10481). These studies imply the importance of controlling size and shape in MgO synthesis for its applications; it is not only the surface area that matters, but the surface chemistry of particle shape and size.

Benzyl alcohol has been found to be a successful medium to tailor metal oxides with well-controlled shape, size and crystallinity under anhydrous conditions, $TiO_2$ nanoparticles of anatase phase in 4-8 mn size range (Niederberger, M. et al. *Chemistry of Materials* 2002, 14, 4364-4370). Vanadium oxide nanorods and tungsten oxide nanoplatelets with identical morphology (Niederberger, M. et al., Journal of the American Chemical Society 2002, 124, 13642-13643) were synthesized in this medium by Stucky and co-workers from metal chloride pre-cursors. Bimetallic oxides of Perovskite structured $BaTiO_3$, $BaZrO_3$, $LiNbO_3$ (Niederberger, M. et al. *Angewandte Chemie-International Edition* 2004, 43, 2270-2273) and $SrTiO_3$, $(Ba, Sr)TiO_3$ nanoparticles (Niederberger, M. et al., *Journal of the American Chemical Society* 2004, 126, 9120-9126) with controlled particle size and high crystallinity have also been prepared through a suggested C—C bond formation mechanism using metal alkoxides as the starting materials. In all these studies, anhydrous conditions are crucial for the formation of metal oxide nanoparticles, while no selectivity in surface growth was found.

OBJECT OF THE INVENTION

It is therefore the object of the invention to provide for a process to prepare a novel form of periclase MgO possessing the (111) crystallographic planes as a primary surface as well as such novel periclase MgO material itself.

SUMMARY OF THE INVENTION

According to the invention, this problem is solved by periclase MgO having a nanosheet structure, the distance of the lattice planes in HRTEM when imaging the nanosheets edge-on being 0.24-0.25 nm, and having the HRTEM images of FIGS. 7a and b and 8a and b and the BF-TEM image of FIG. 6.

Preferably, the nanosheets have a thickness of less than 10 nm, most preferably between 3 and 5 nm.

The invention is also directed to a method for preparing periclase MgO with the respective microscopy data and images, comprising the following steps: preparation of $Mg(OCH_3)_2$ in methanol solution; adding 4-methoxy benzyl alcohol (MBZ) or 4-nitro benzyl alcohol (NBZ) or a mixture thereof in a ratio of Mg to MBZ and/or NBZ of at least 1; addition of a water/methanol mixture to the system; and solvent removal and calcination in air of said mixture.

Preferably, the ratio of Mg to MBZ and/or MBZ is between 1:1 to 1:3, most preferably about 1:2.

When MBZ is used in step (a) the solvent removal is preferably accomplished by a supercritical treatment. Most preferably, toluene is added to the mixture for the supercritical treatment.

Here, we report for the first time a preferential growth of nanoscale plate-like magnesium oxide possessing (111) planes as a main surface [herein designated as IUB-Z] in 4-nitro-/methoxyl-benzyl alcohol. In our system, a water/methanol mixture was added to hydrolyze the magnesium methoxide.

Herein, we provide a convenient way to prepare nanoplates of MgO (IUB-Z), whose thickness is preferably less than 10 nm, most preferably between 3 and 5 nm. More interestingly, to the major surface of the "plate" is the highly ionic (111) surface. To synthesize these MgO nano-plates, a stoichiometric amount of 4-nitro-/4-methoxyl-benzyl alcohol was added to a 10 wt. % $Mg(OCH_3)_2$ in methanol solution, followed by addition of water/methanol mixture to the system and subsequent hydrothermal treatment and calcination in air. Here 4-nitro-/4-methoxyl-benzyl alcohol were chosen for their strong interaction with the inorganic precursor Mg(OH)$(OCH_3)_2$ and similarity with toluene in structure, in which the two methanol molecules can be changed by two benzyl alcohol molecules, as the latter is a stronger acid than methanol, therefore, the substitution can occur spontaneously after mixing.

Although Klabunde and co-workers have employed a large number of organic solvents with different dielectric constant to the gelation of the $Mg(OCH_3)_2$/methanol mixture, no solvents they have employed are capable of interacting with the inorganic precursor as strongly as those employed for the preparation of MgO nanosheets of the present invention.

BRIEF DESCRIPTION OF THE DRAWINGS

FIGS. 4a and b. BF-TEM images showing larger aggregates and scattered small aggregates of MgO. The majority of the sheet-like nanoparticles are oriented almost parallel to the support film. However, some of the sheets are also imaged edge on.

FIG. 6. BF-TEM image of an isolated nanosheet viewed edge on.

DETAILED DESCRIPTION OF THE INVENTION

In a typical synthesis of this MgO nanosheet structure (IUB-Z), 1.0 g of Mg belt was cleaned by sand paper and acetone, then the belt was cut into small pieces and dissolved in absolute methanol under a static argon atmosphere. After the Mg belt totally dissolved, 4-methoxy-benzyl alcohol (MBZ) was added to the mixture in the ratio Mg:MBZ=2 (molar ratio). After stirring for 5 h, H$_2$O (molar ratio of 2 with respect to Mg) was dissolved into 30.0 ml methanol and was added dropwise into the system under stirring, the mixture was stirred for 12 h before being transferred to an autoclave. The autoclave containing the reaction mixture was purged with Ar for 10 min, and then a pressure of 10 bars Ar was imposed before heating starts. The mixture was heated to 265° C. and kept for 15 h continuously, then the vapor inside was vented (thereby removing the solvent in the supercritical state). A dry white powder was collected and subsequently calcined with a ramp rate of 3° C./min to 500° C., then maintained at 500° C. for 6 h. The ultra-fine white powder produced from the above contains solely IUB-Z, the MgO nanosheets possessing the (111) crystallographic planes as the main surface.

Further examination of various synthetic conditions shows that many parameters are variable: Mg:H$_2$O, Mg:MBZ, Mg concentration in methanol can vary greatly while the structure of the final products remains the same. Variation of the above ratio from 1:1 to 1:3 results in no obvious change in the final products. Further, the system was also heated in solvent-thermal conditions, i.e., from 100° C. to 265° C. The dispersion of these nanosheets is improved upon increased temperature, while at lower temperatures, aggregation occurs, surface area decreases as aggregation occurs accordingly. Addition of toluene into the mixture will help the dispersion of the nanosheets and does not change the surface orientation and shape. While more meso-pores were created when 40 ml of toluene was added to the mixture before supercritical treatment, the 4-nitro-benzyl alcohol (NBZ) templated mixture can not be supercritically treated because the nitro groups can be reduced by the alcohol and subsequently form coke. Compared with supercritically treated IUB-Z, the solvent-thermally treated samples have a smaller surface area, 4-methoxyl-BZ and 4-nitro-BZ templated IUB-Z have a surface area of 96 and 93 m$^2$/g, respectively, however, the 4-methoxyl-BZ templated IUB-Z from supercritical treatment has a surface area of 198 m$^2$/g. Addition of toluene does not affect the surface area, which creates a IUB-Z MgO with a surface area of 196 m$^2$/g, but does seem to affect the agglomerate macrostructure.

The MgO nanosheets possessing the 111 plane have been characterized by a combination of bright-field transmission electron microscopy (BF-TEM), high-resolution transmission electron microscopy (HRTEM) and electron diffraction with additional evidence of the sample purity from local EDX measurements.

Figure 1:
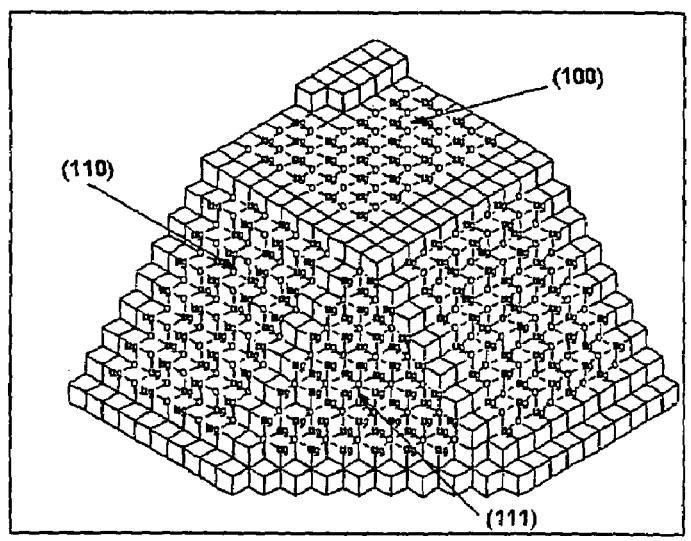
FIG. 1. Index planes of MgO.
Figure 2:
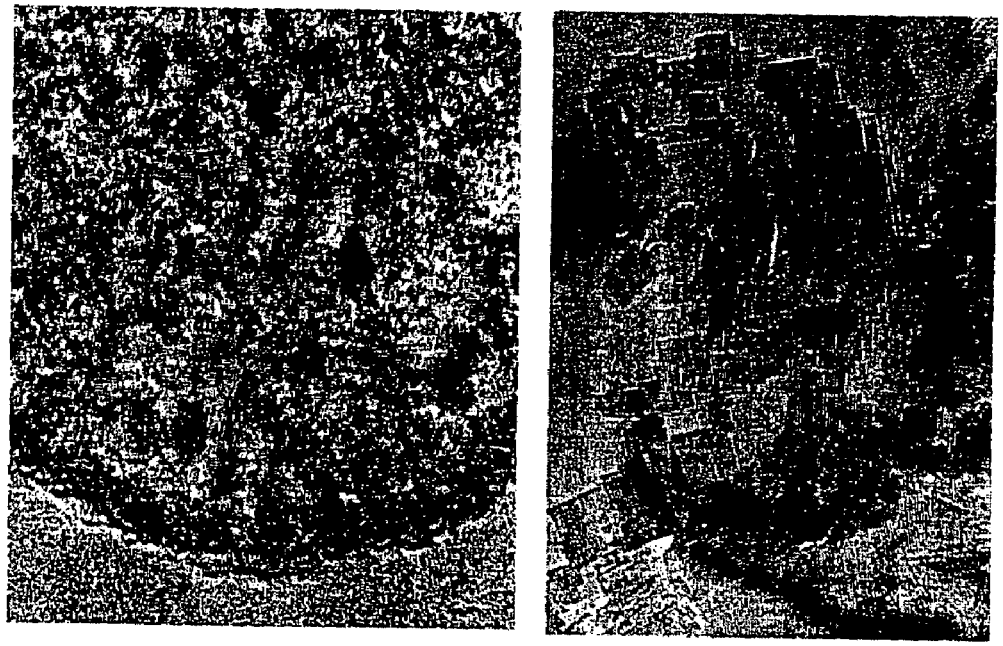
FIG. 2. CP MgO (left) demonstrates interconnected MgO domains about 2 nm with lattice spacing of 1.48 Å, while AP MgO (right) shows monocrystalline particles between 1 and 3 nm with a lattice spacing of 2.1 Å corresponding to the 001 plane.
Figure 3:
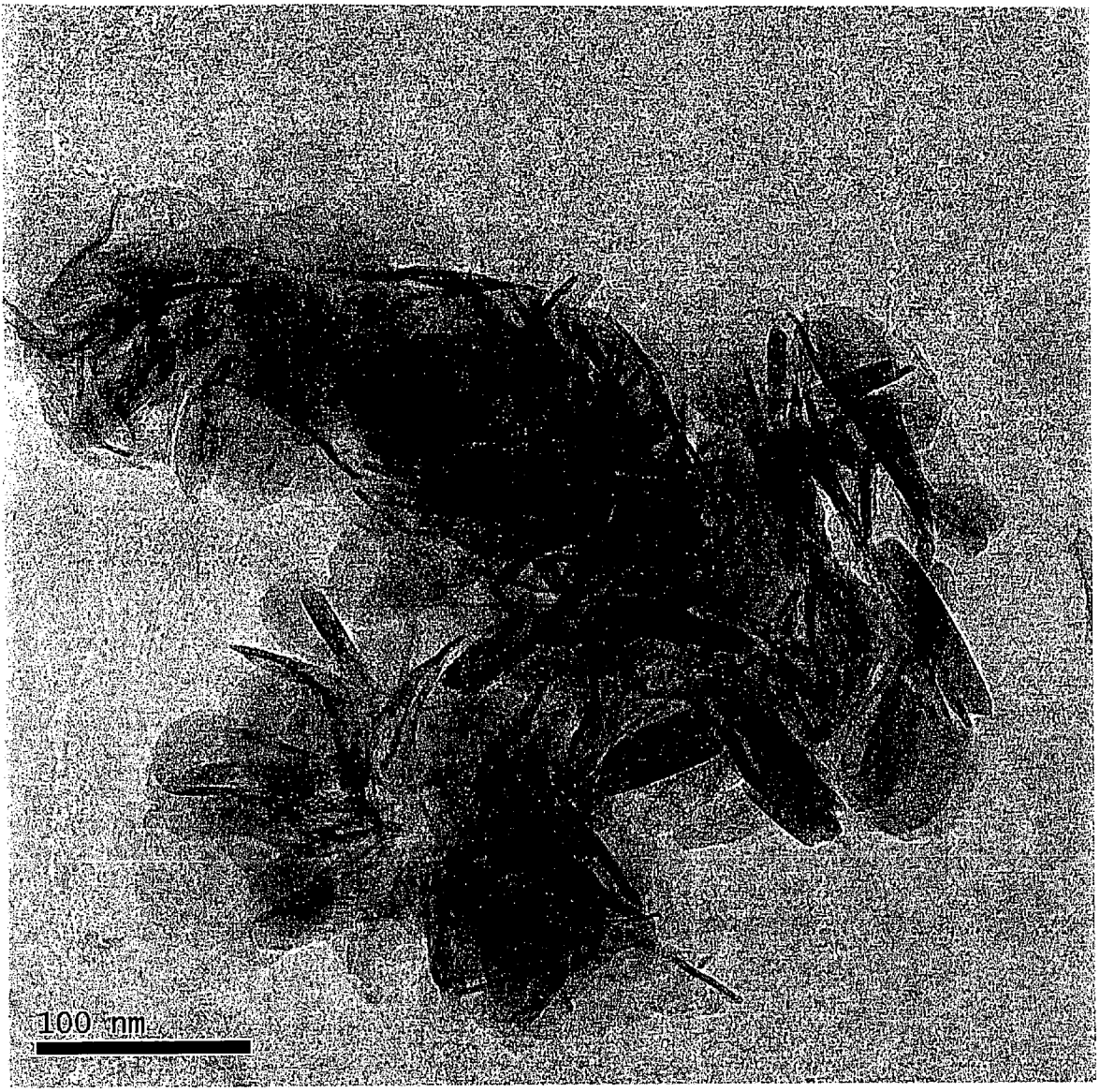
FIG. 3. BF-TEM image of an aggregate of plate-like $Mg(OH)(OCH_3)_2$ crystals before calcination.
Figure 4A:
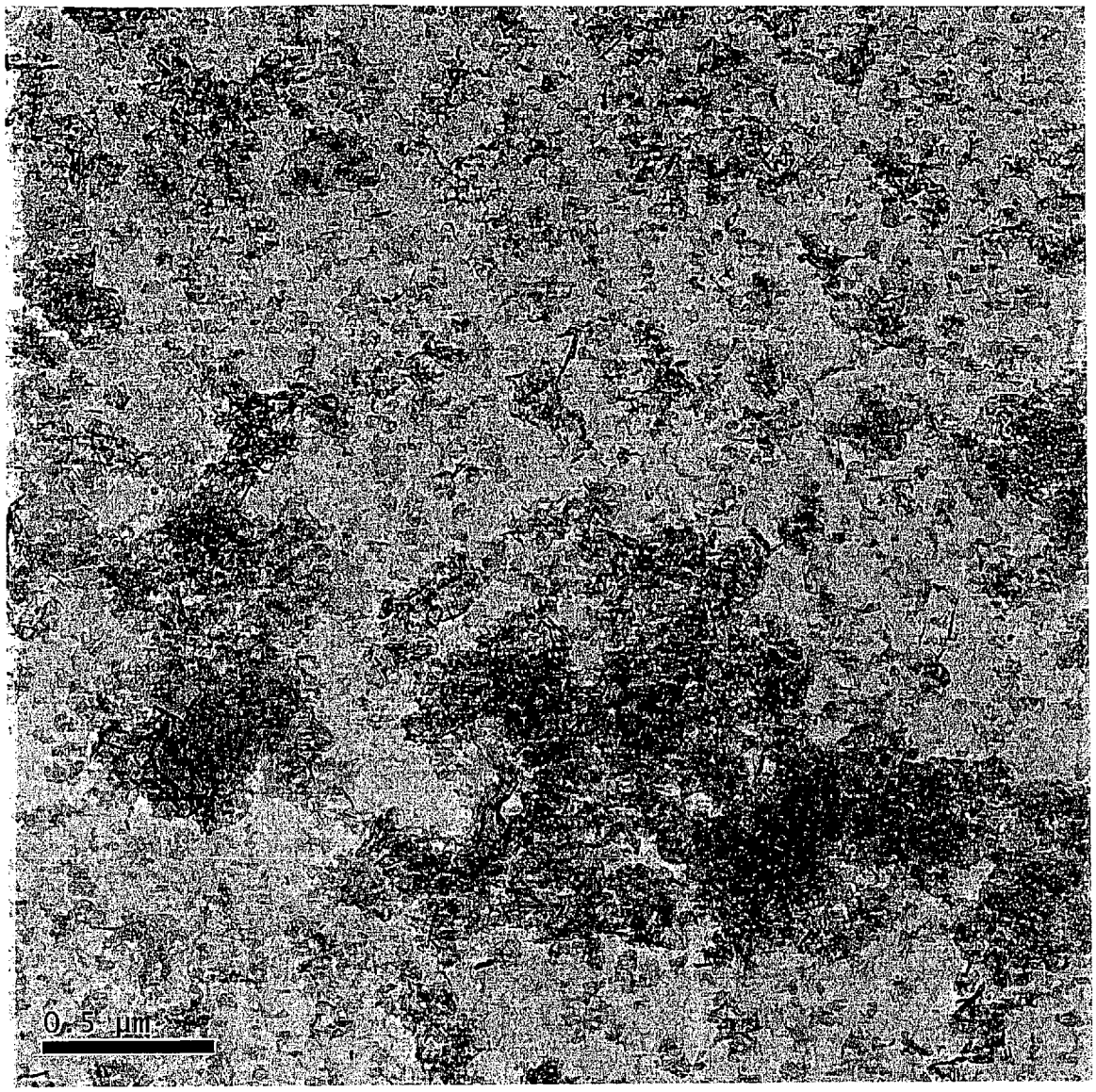
Figure 4B:
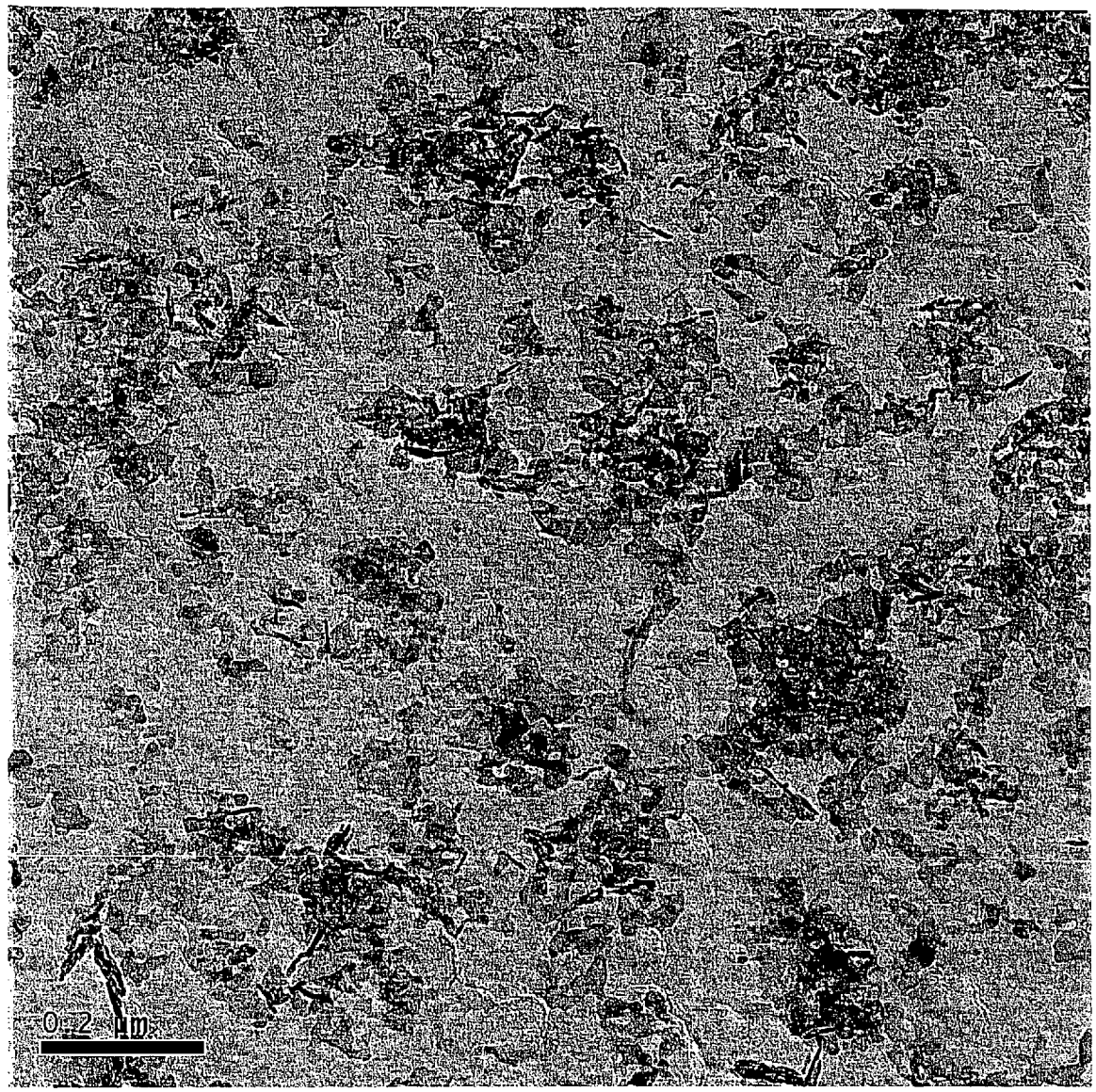

BF-TEM of the Mg(OH)(OCH$_3$)$_2$ precursor and the calcinated MgO samples reveals that the material crystallizes forming nanosheets with a typical diameter of 50-200 nm and a thickness of typically 3-5 nm (see FIGS. 3 and 4a and b).

Figure 5A:
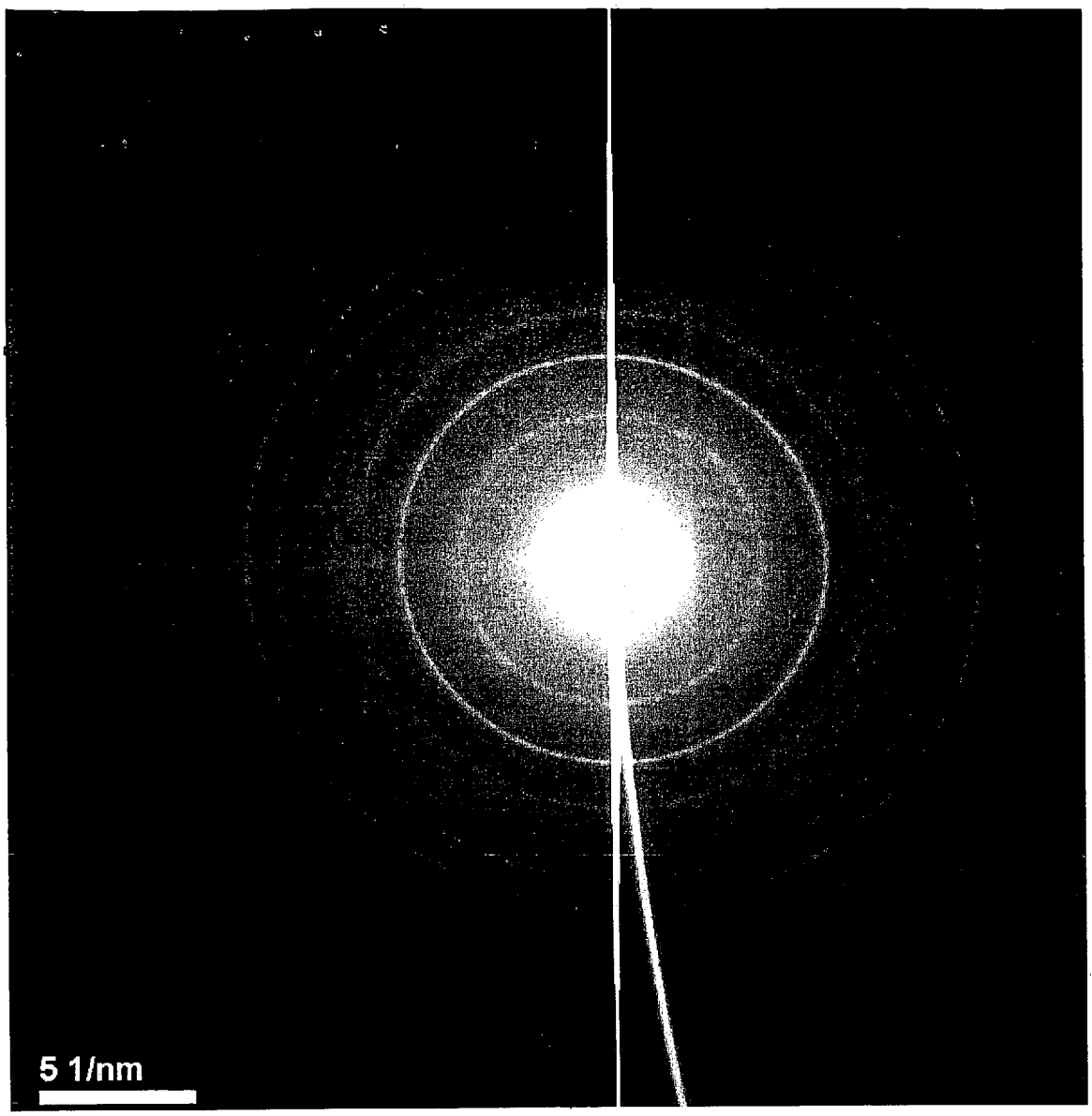
FIG. 5a. Electron diffraction pattern of randomly oriented aggregates of MgO nanosheets exhibiting the typical lattice spacings for periclase.

Electron diffraction from thin MgO aggregates proves that the MgO nanosheets crystallize in the periclase structure. The observed lattice spacings are in excellent agreement with the literature known d-spacings for periclase (Sasaki, S. et al. Proc. Jpn. Acd., 1979, 55, 43) (see FIGS. 5a and b and, Table 1).

TABLE 1

| d observed [Å] | d calculated [Å] | Indexing |
| --- | --- | --- |
| 2.439 | 2.435 | 111 |
| 2.105 | 2.108 | 200 |
| 1.486 | 1.491 | 220 |
|  | 1.271 | 311 |
| 1.215 | 1.217 | 222 |
| 1.053 | 1.054 | 400 |
|  | 0.967 | 331 |
| 0.942 | 0.943 | 420 |
| 0.861 | 0.861 | 422 |
|  | 0.812 | 333/511 |
| 0.748 | 0.745 | 440 |
| 0.705 | 0.713 | 531 |
|  | 0.703 | 600/442 |
| 0.669 | 0.667 | 620 |
| 0.640 | 0.643 | 533 |
|  | 0.636 | 622 |

Figure 5B:
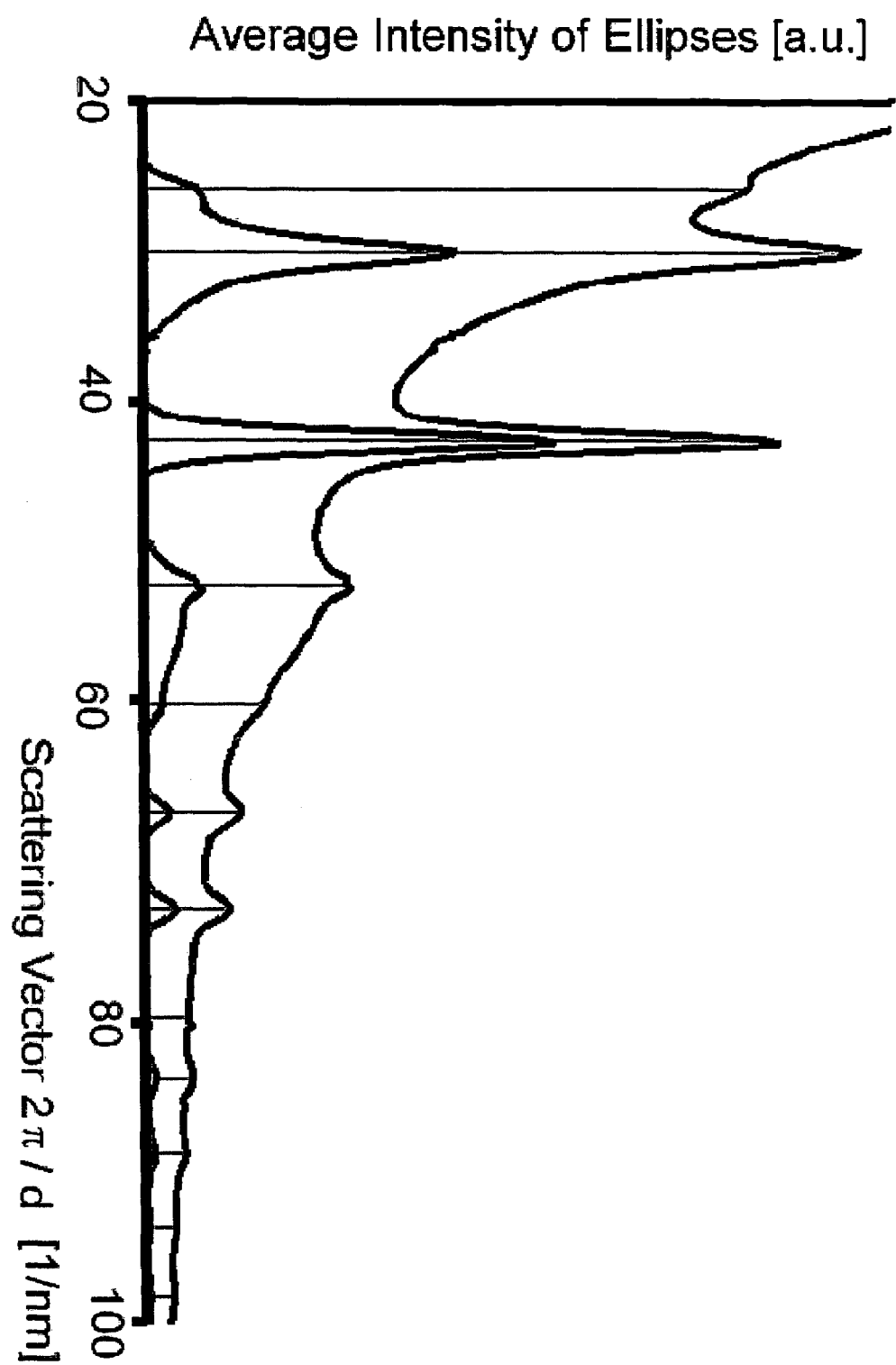
FIG. 5b. Rotationally averaged line profile of the electron diffraction pattern of FIG. 5a. The high intensity of the 220 and 422 reflexes indicated a slight preferential orientation of the nanosheets along the [111] zone.

Table 1. Electron diffraction of MgO nanosheets. Analysis of the peak position in the electron diffraction powder pattern of a thin MgO aggregate (FIG. 5b) is in excellent agreement with the symmetry allowed lattice spacings in periclase. The absolute lattice spacings were calibrated with respect to gold nanoparticles and the camera length fine tuned for optimum agreement by less than 2%.

Figure 7A:
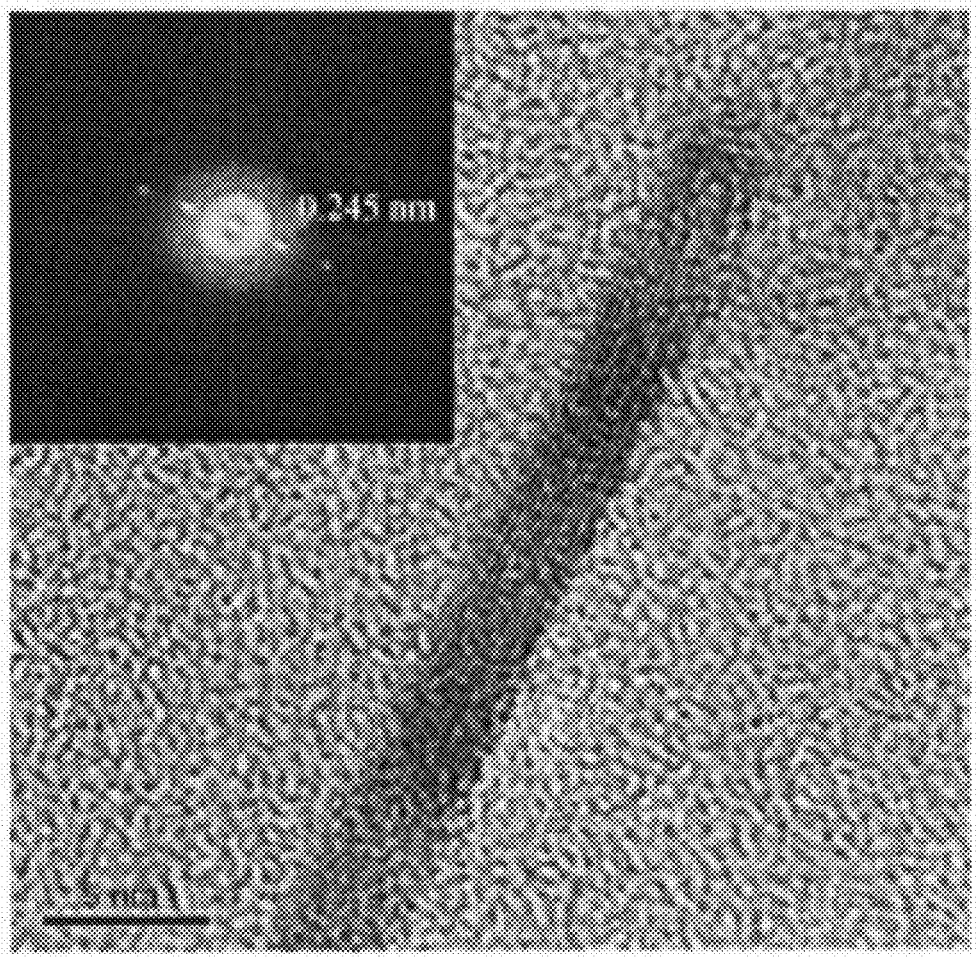
FIG. 7a. HRTEM image and local FFT of the isolated MgO nanosheet in FIG. 6. The observed lattice spacings of 0.25 nm correspond to a set of (111) lattice planes forming the main surface of the crystal.
Figure 7B:
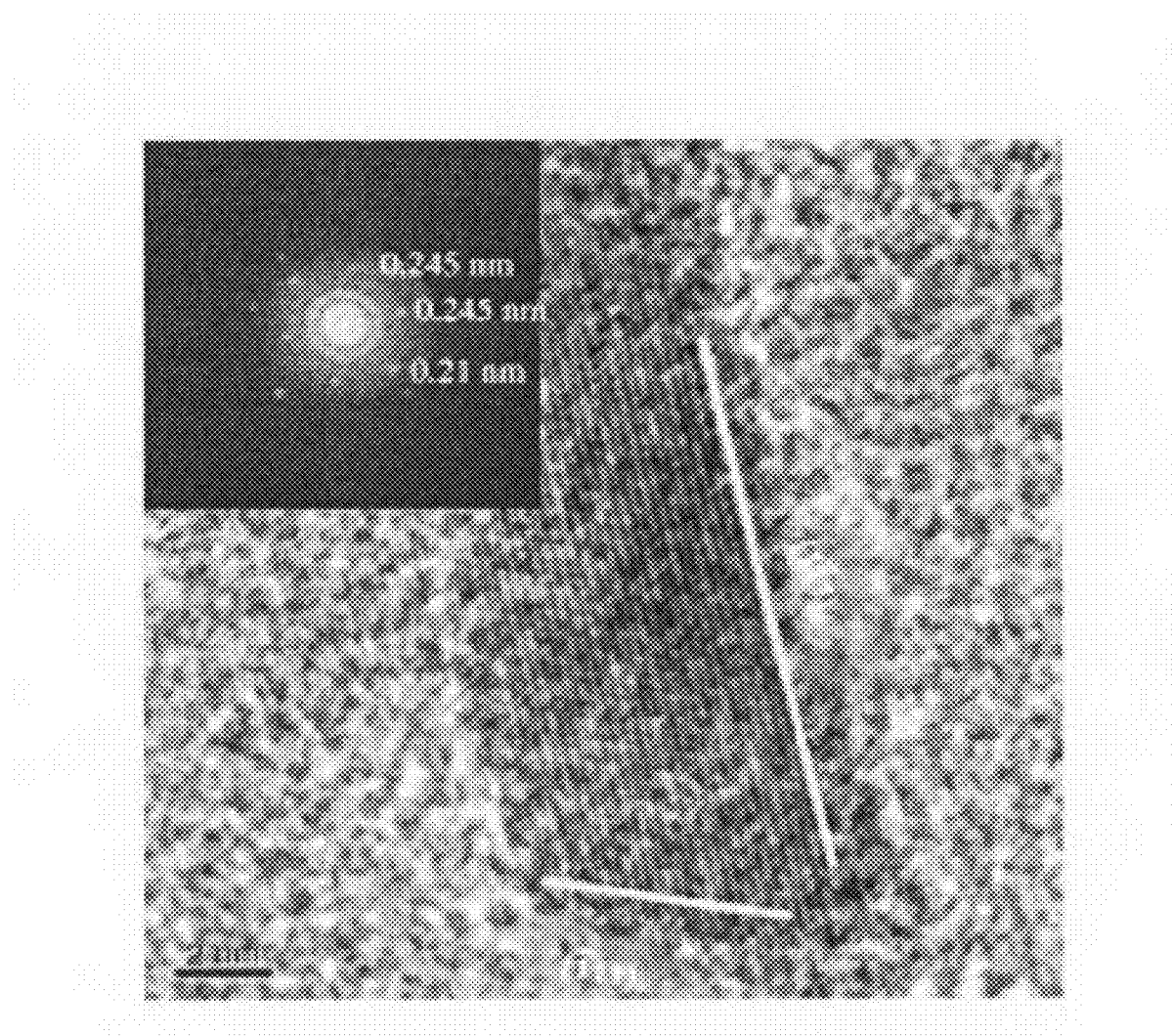
FIG. 7b. HRTEM image and local FFT of an isolated MgO nanosheet. The observed lattice spacings of 0.25 nm correspond to two sets of (111) lattice planes forming the main surfaces of the crystal.
Figure 8A:
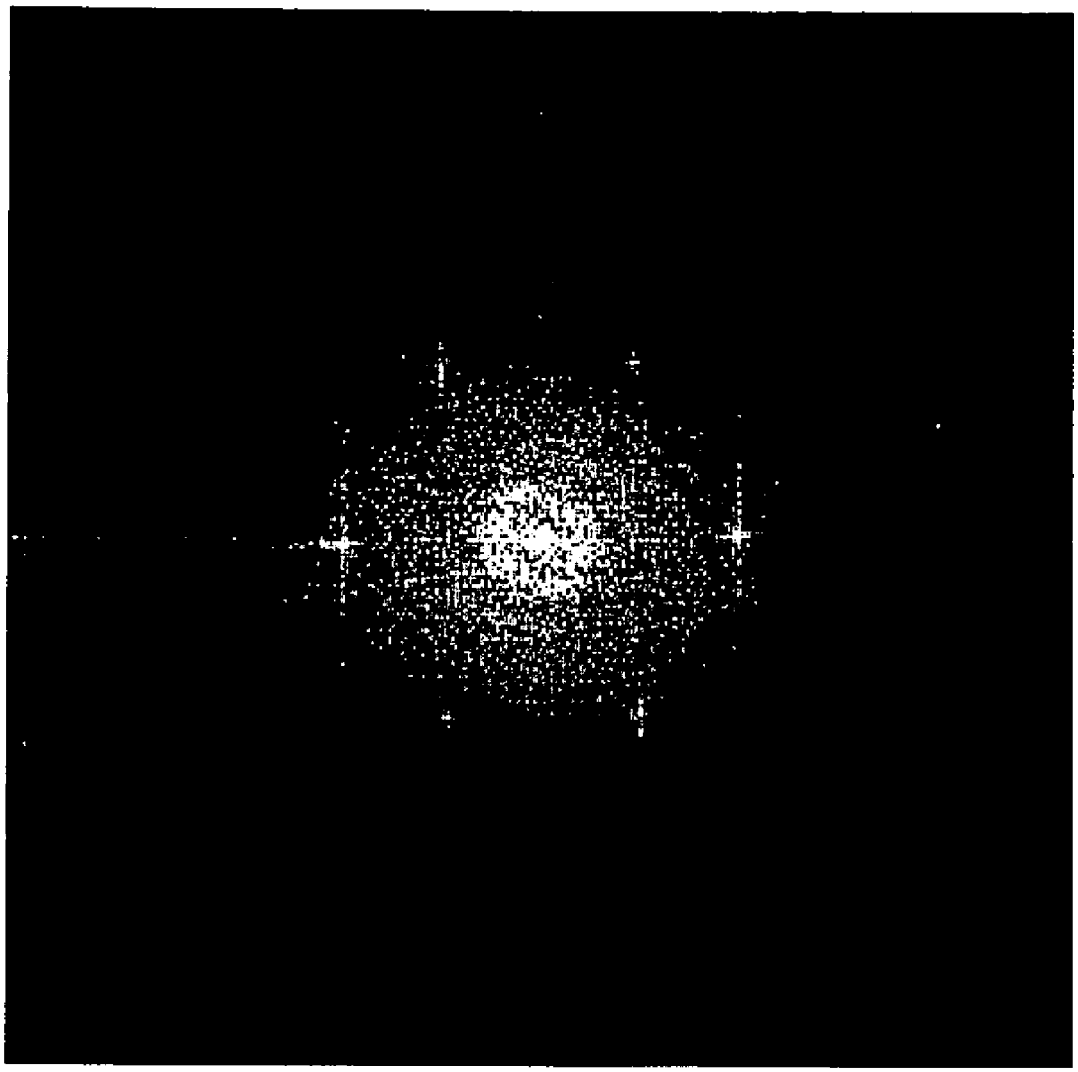
FIGS. 8a and b. HRTEM image and local FFT of MgO nanosheets oriented parallel to the carbon support film. The FFT reveals the characteristic lattice spacings and angles of the [111] zone indicative that the sheets lay on the (111) lattice plane.
Figure 8B:
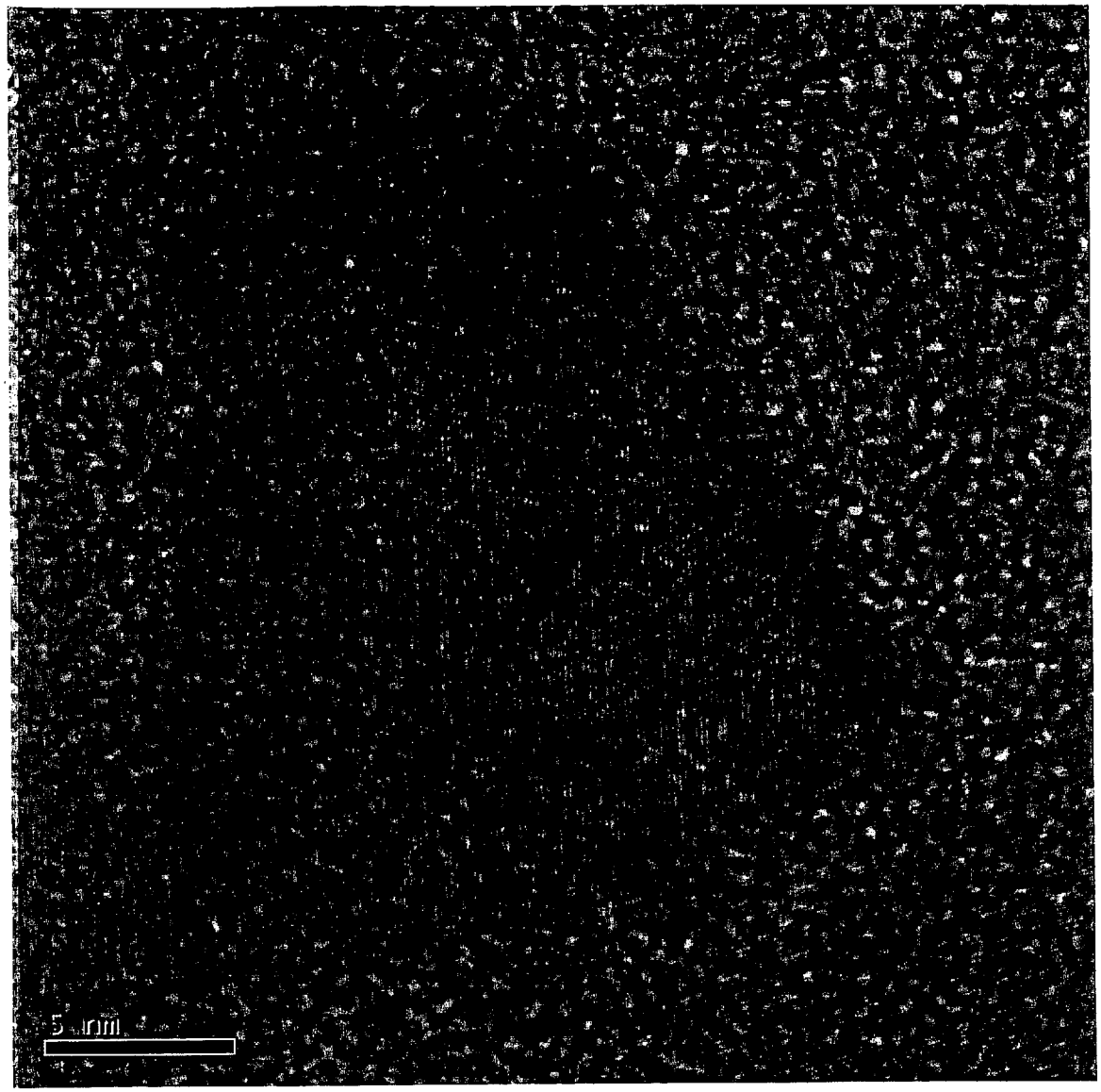

HRTEM analysis of isolated nanosheets shows that the main surface of the nanosheets is the (111) lattice plane in MgO. When imaging the nanosheets edge on, the HRTEM images exhibit lattice fringes with a distance of 0.24-0.25 nm, being typical for the (111) plane forming the surface of the nanosheets. When imaging isolated nanosheets oriented parallel to the support film, the HRTEM images typically exhibit the characteristic lattice fringes of the [111] zone, indicating that the sheets lay on the (111) plane perpendicular to the [111] zone (see FIGS. 7a and b, and 8a and b).

Figure 9:
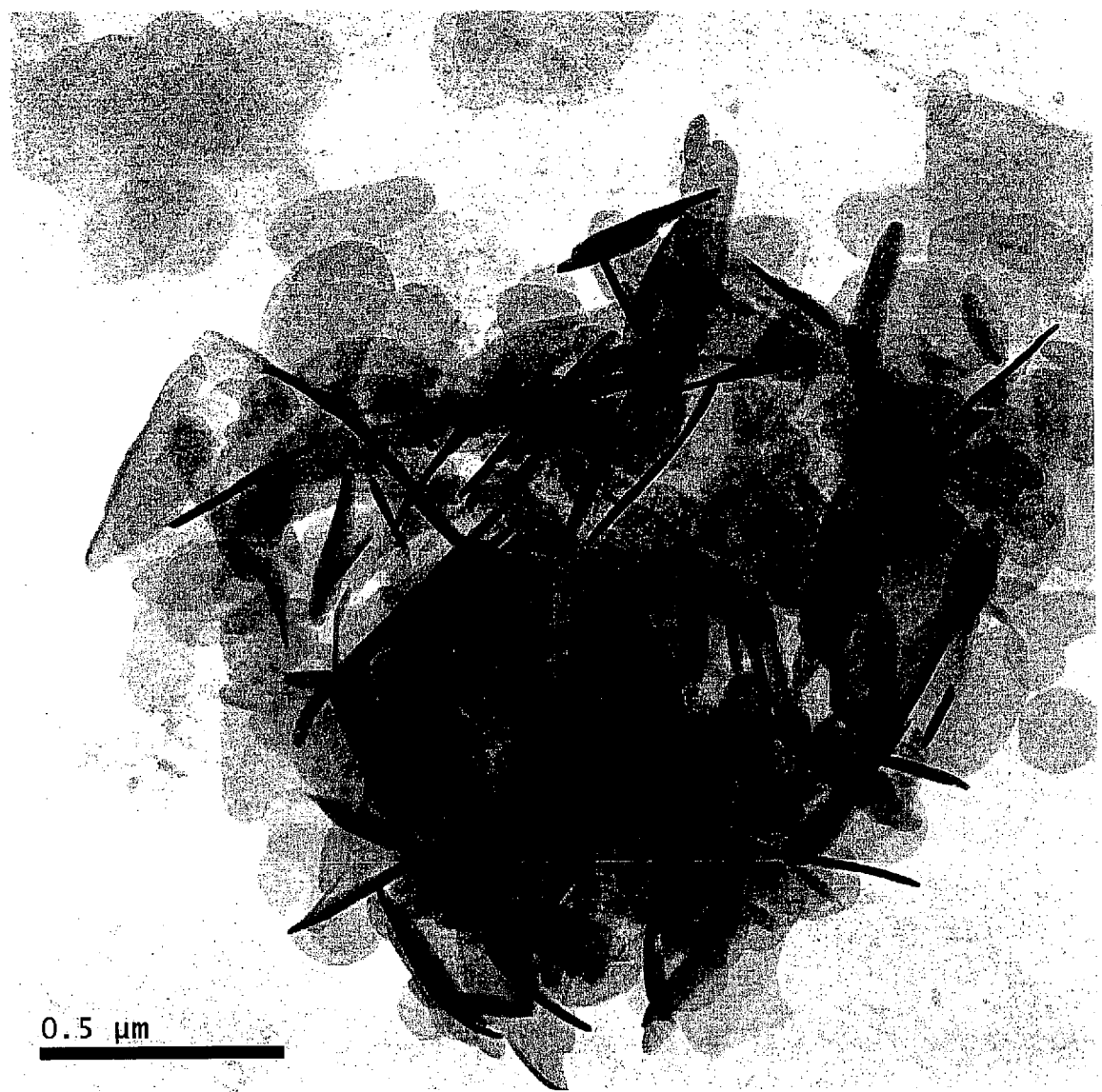
FIG. 9. BF-TEM image of an aggregate of Mg(OH)$(OCH_3)$ nanosheets prepared with toluene added to the mixture after supercritical treatment.
Figure 10:
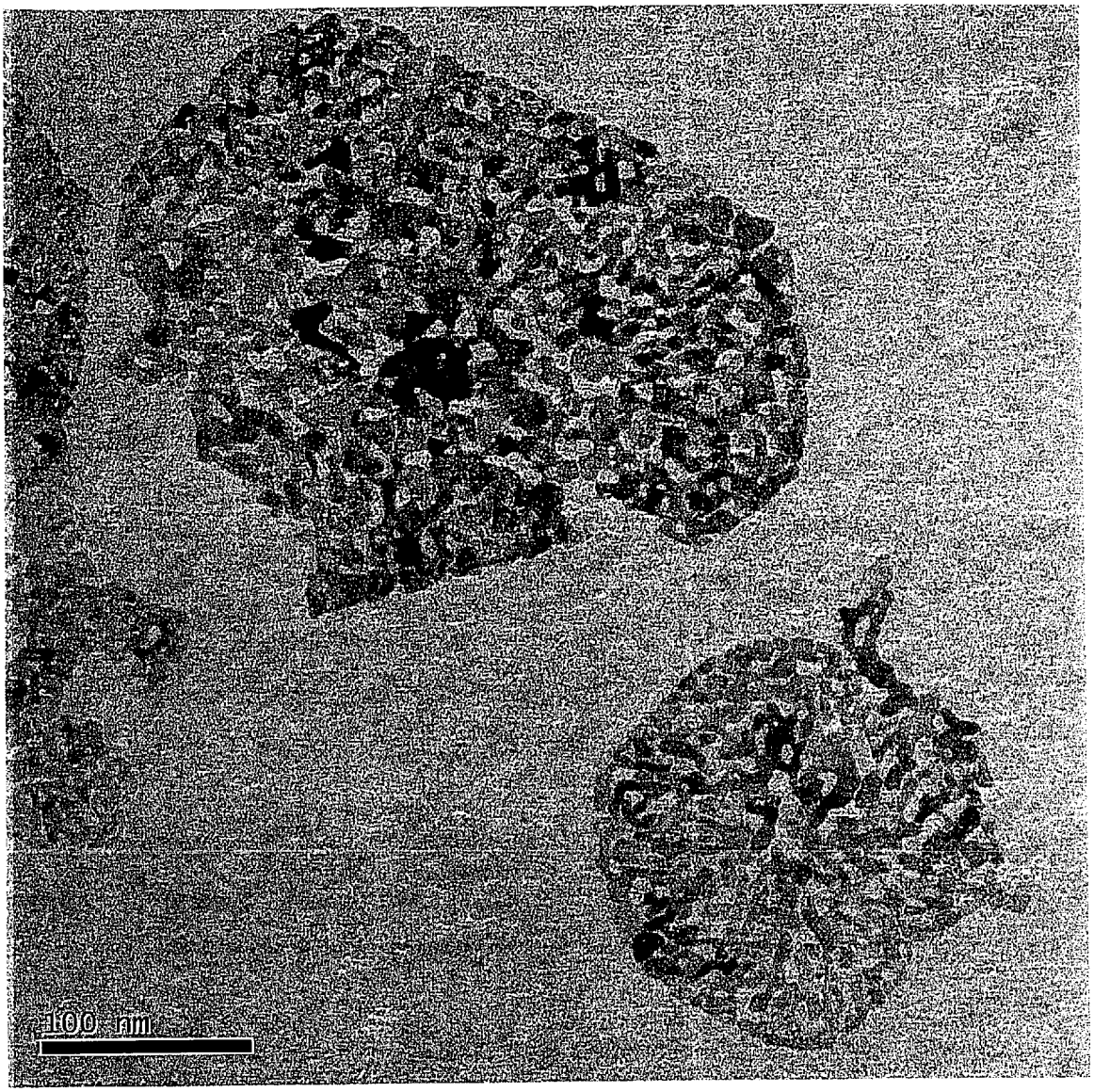
FIG. 10. BF-TEM image of highly porous isolated MgO nanosheets of MgO prepared by calcination of Mg(OH)(OCH$_3$) nanosheets prepared with toluene.
Figure 11A:
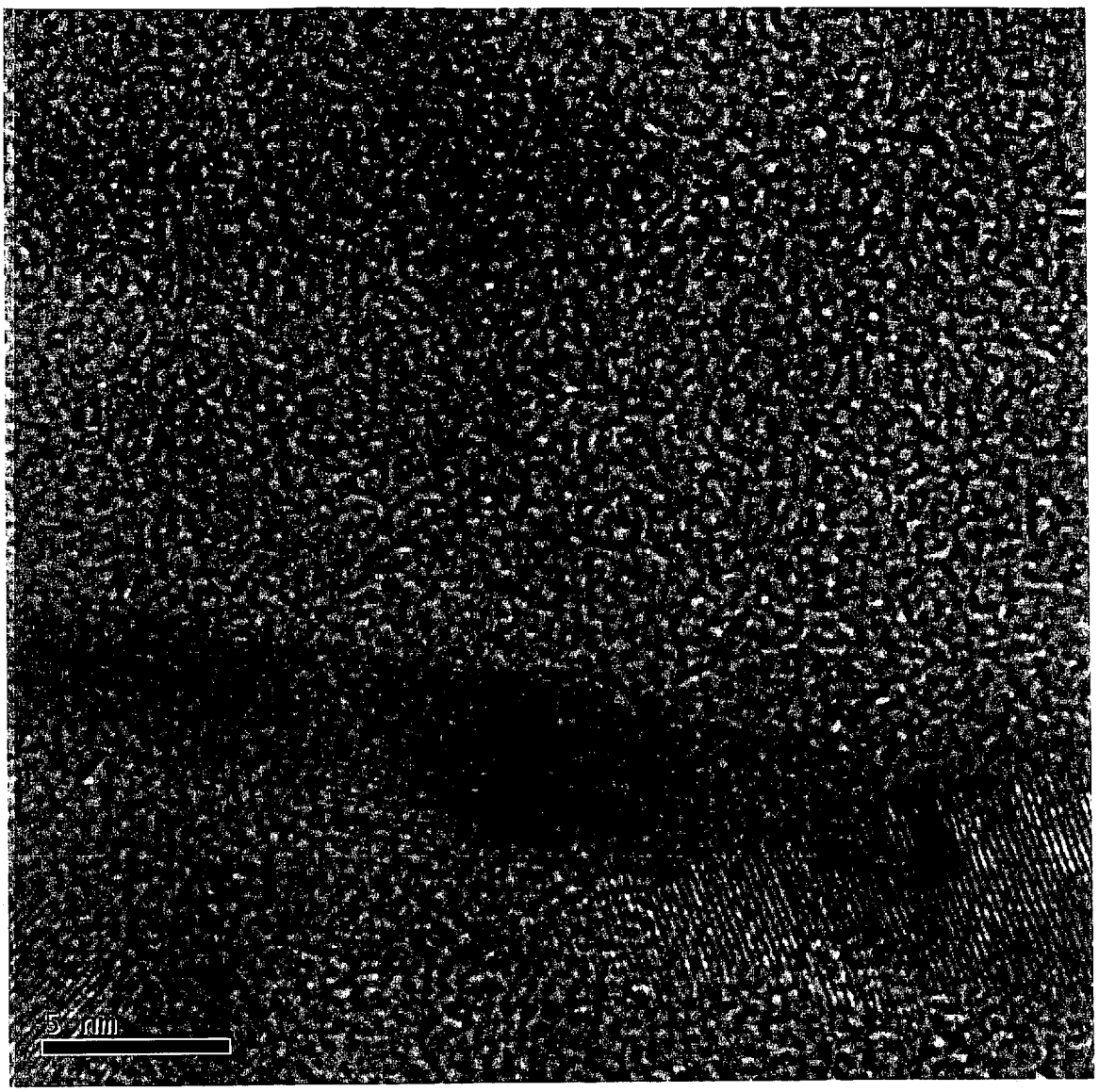
FIGS. 11a and b. HRTEM image and local FFT of an isolated MgO nanosheet (by calcination of Mg(OH)(OCH$_3$) prepared with toluene). The observed lattice spacings of 0.245 nm correspond to the (111) lattice planes forming the main surface of the crystal.
Figure 11B:
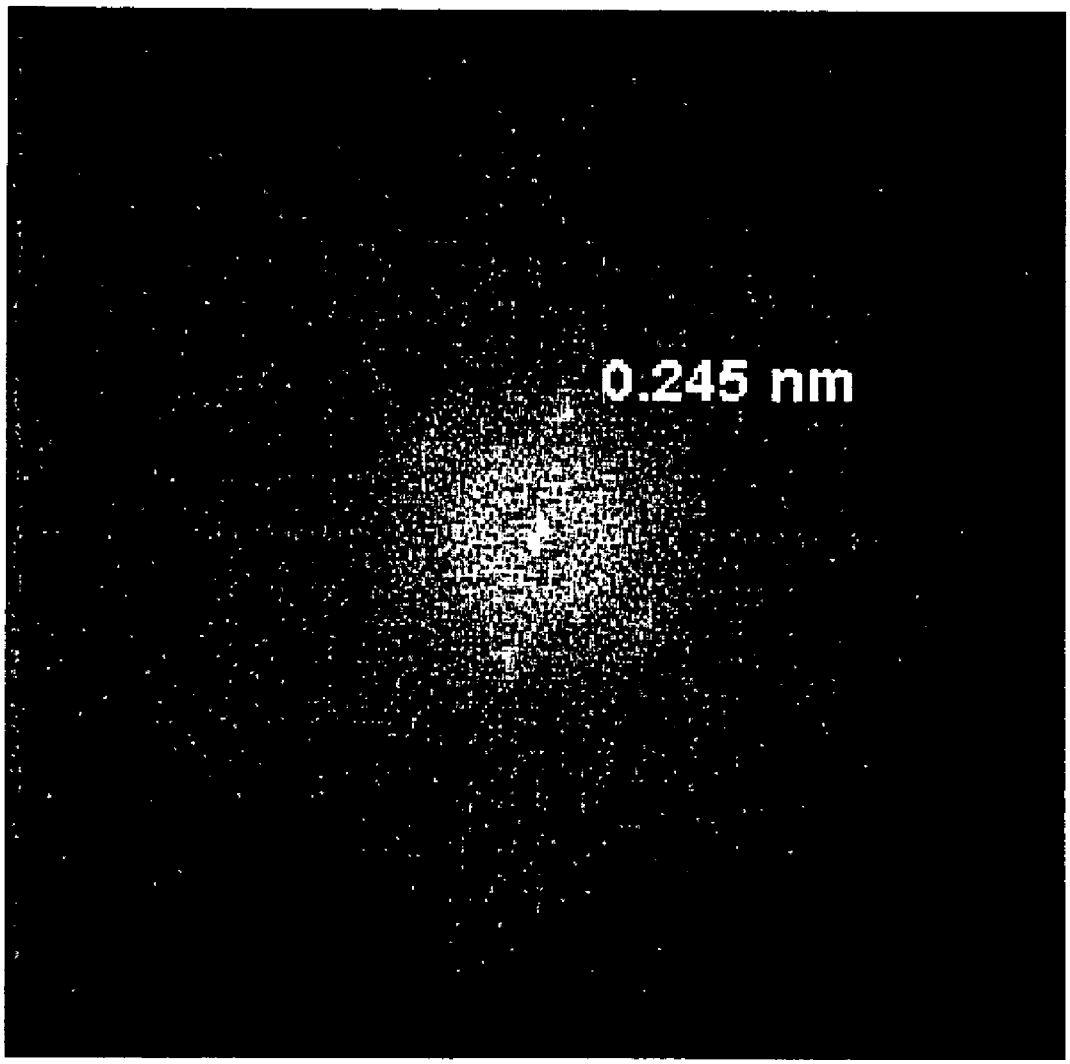
Figure 12A:
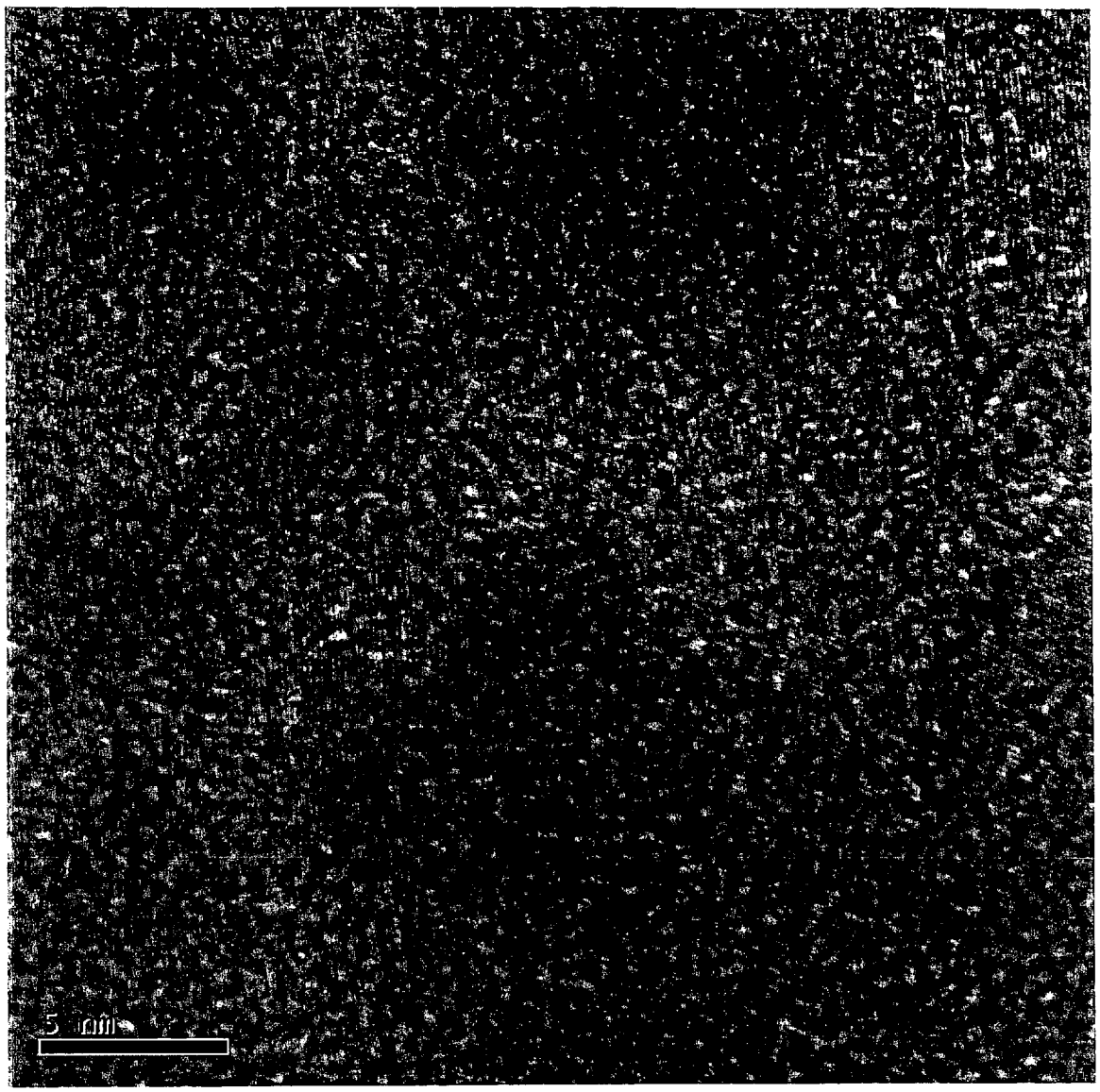
FIGS. 12a and b. HRTEM image and FFT of a porous MgO nanosheet (by calcination of Mg(OH)(OCH$_3$) prepared with toluene) oriented parallel to the carbon support film. The FFT reveals the characteristic lattice spacings and angles of the [111] zone indicative that the sheets lay on the (111) lattice plane.
Figure 12B:
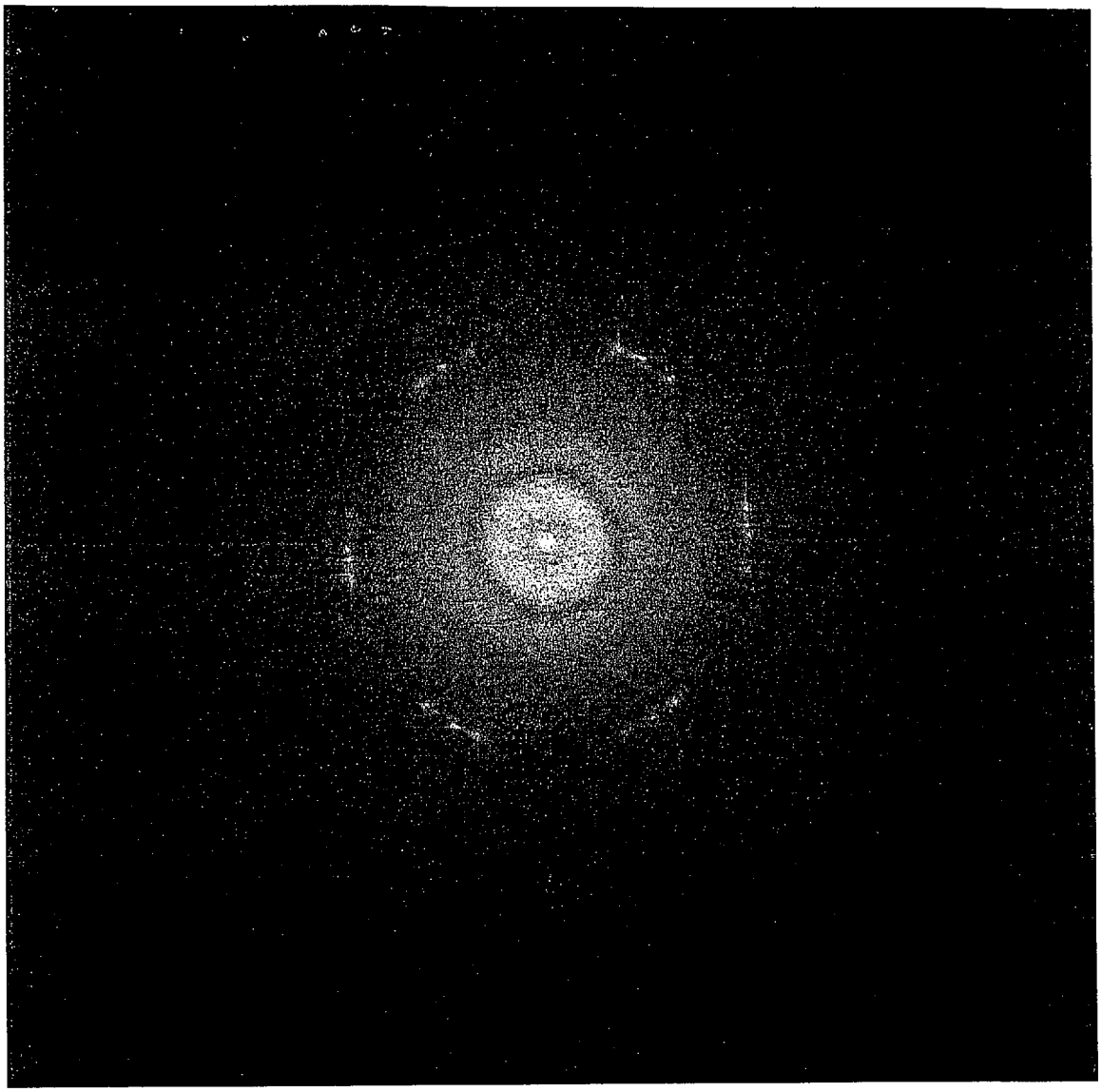
Figure 13:
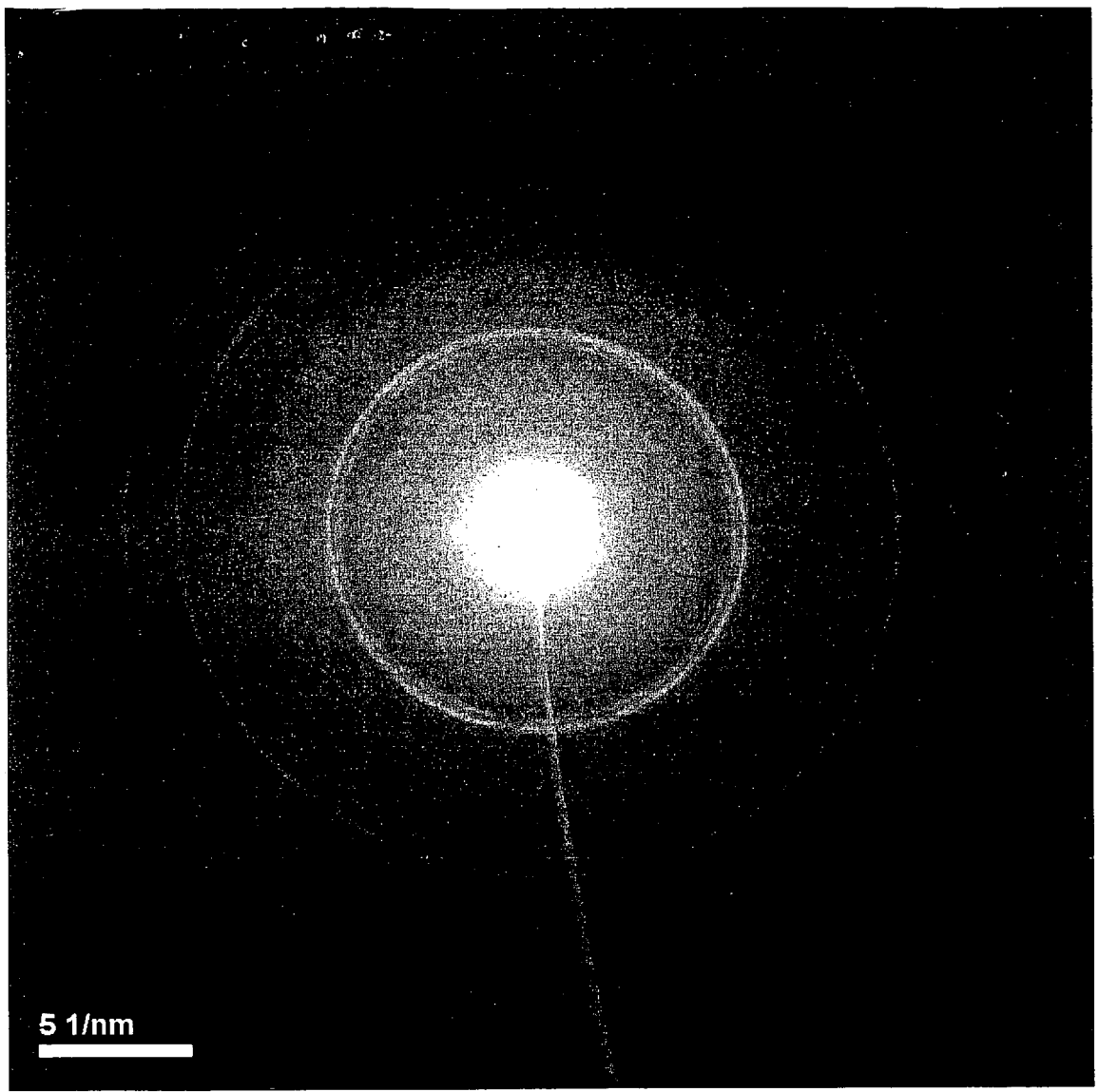
FIG. 13. Electron diffraction pattern of a porous MgO nanosheet oriented parallel to the carbon support film. The electron diffraction pattern mainly exhibits the (220), (422), and (440) reflections indicating that the porous MgO nanosheet is oriented along the [111] zone with the different crystallites rotated with respect to each other.—During sample preparation, the porous MgO nanosheets were partially hydrolyzed to Mg(OH)$_2$ giving rise to the additional reflections in the electron diffraction pattern.

The basic TEM analysis for samples prepared with toluene added to the mixture is the same as without the toluene. However, the nanosheets are typically larger with a thickness of up to 25 nm and a diameter of up to 500 nm. During calcination, these larger sheets do not form uniform MgO sheets, but highly porous sheets of MgO (FIG. 10). Nevertheless, these porous sheets exhibit the same preference for the (111) lattice plane forming the surface of the nanosheets (see FIGS. 9, 10, 11a and b, 12a and b, and 13). As can be seen from FIG. 13, mainly lattice spacings corresponding to the (220), (422) and (440) planes are observed in the diffraction pattern indicating that despite the in-plane rotational of the nanocrystals, all nanocrystals are oriented along the 111 zone. Part of the MgO has been hydrolyzed during sample preparation giving rise to an additional weaker set of 220, 422 and 440 diffraction rings for $Mg(OH)_2$.

Local EDX measurements acquired in STEM mode over an area of about 2 $\mu m^2$ with thin aggregates of the calcinated MgO nanosheets on carbon support film show that only O and Mg are present in the sample in addition to C from the carbon support film and Cu from the copper support grid. Quantification of the O and Mg intensities reveals a composition close to 1:1 (52 at-% O, 48 at-% Mg) in agreement with MgO. Quantification of the O and Mg ratio has been performed using the TIA software package of the FEI Tecnai after empirical background correction of the EDX spectrum (background corrected integrated intensities 0: 3500±600 counts, Mg: 7600±900 counts) with an absorption correction for the EDAX S-UTW detector but without thickness correction.

Figure 14A:
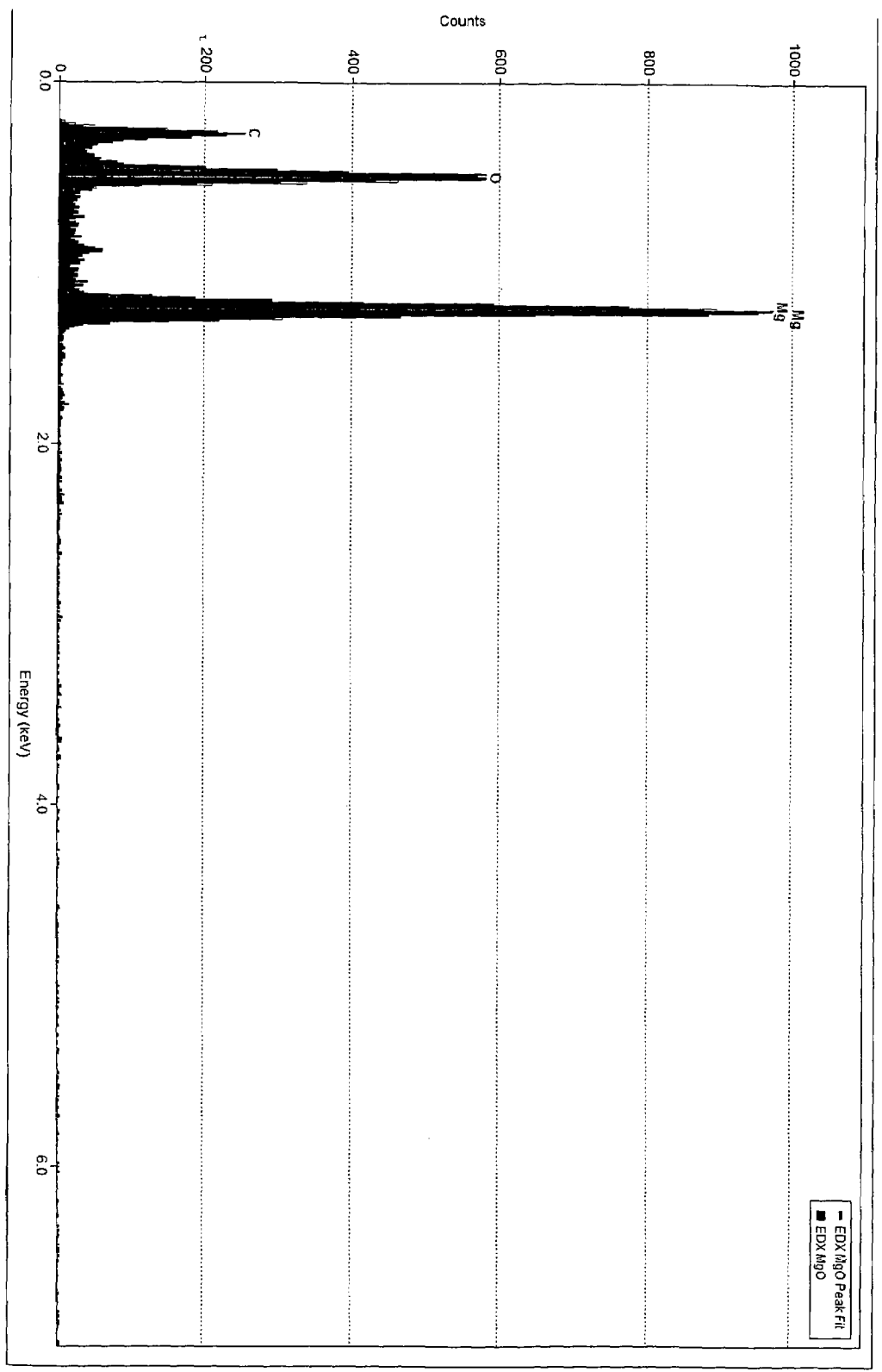
FIGS. 14a and b. EDX spectra of MgO and the Mg(OH)(OCH$_3$) obtained by averaging the EDX signal of an area of 2 μm$^2$ with thin aggregates of nanosheets. The spectra only exhibit Mg and O in addition to C and Cu from the sample support.
Figure 14B:
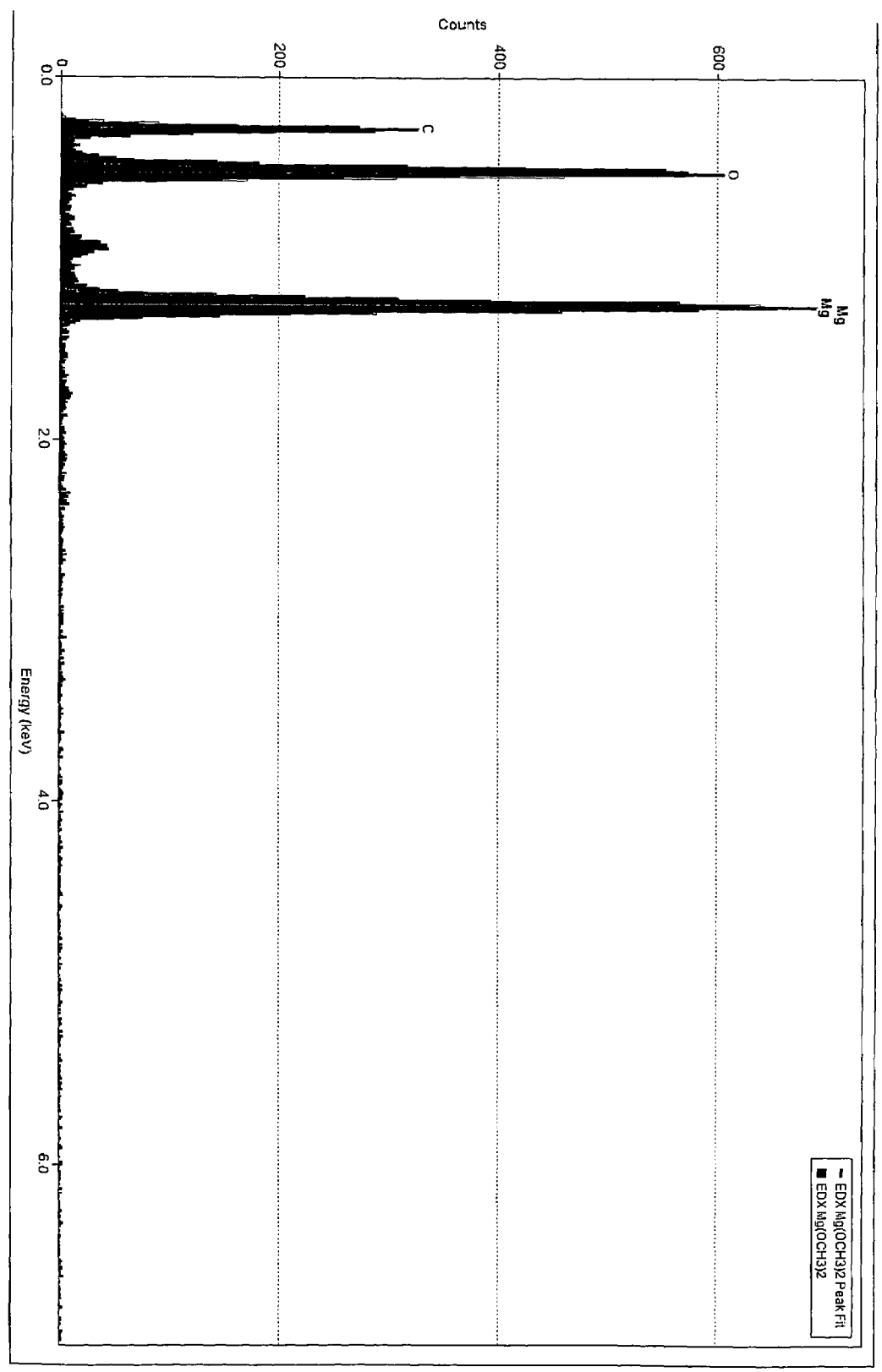

The analogous EDX analysis of the $Mg(OH)(OCH_3)_2$ precursor material reveals a composition of Mg:O=1:2 (66 at-% O, 34 at-% Mg, background corrected integrated intensities 0: 3300±600 counts, Mg: 4900±700 counts) in agreement with $Mg(OCH_3)_2$, $Mg(OH)(OCH_3)$ or $Mg(OH_2)$—the carbon content cannot be determined in this EDX analysis due to the carbon support film (see FIGS. 14a and b).

The features disclosed in the foregoing description, in the claims and in the drawings may, both separately and in any combination thereof, be material for realizing the invention in diverse forms thereof.

Figure 6:
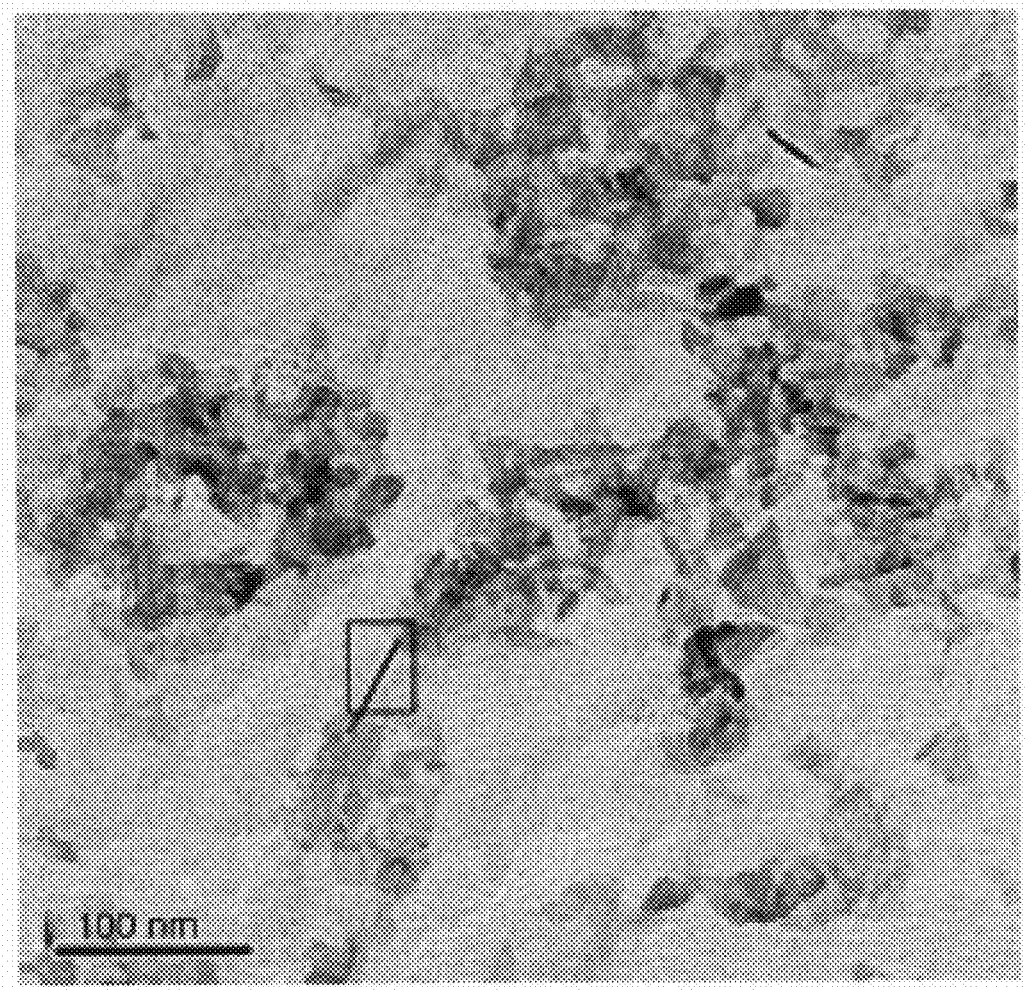

The invention claimed is:

1. Periclase MgO having a nanosheet structure, the distance of the lattice planes in high resolution transmission electron microscopy (HRTEM) when imaging the nanosheets edge-on being 0.24-0.25 nm, and having the HRTEM images of FIGS. 7a and b and 8a and b and the bright field transmission electron microscopy (BF-TEM) image of FIG. 6.

2. MgO according to claim 1, wherein the nanosheets have a thickness of less than 10 nm.

3. MgO according to claim 2, wherein the nanosheets have a thickness of between 3 and 5 mn.

* * * * *

UNITED STATES PATENT AND TRADEMARK OFFICE
CERTIFICATE OF CORRECTION

| | | |
|---|---|---|
| PATENT NO. | : 7,608,238 B2 | Page 1 of 1 |
| APPLICATION NO. | : 11/356314 | |
| DATED | : October 27, 2009 | |
| INVENTOR(S) | : Richards et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 807 days.

Signed and Sealed this

Twelfth Day of October, 2010

David J. Kappos
*Director of the United States Patent and Trademark Office*